(12) United States Patent
Borate et al.

(10) Patent No.: US 9,447,082 B2
(45) Date of Patent: Sep. 20, 2016

(54) OPTICALLY ACTIVE FLUCONAZOLE ANALOGUES CONTAINING THIOPHENES AS ANTIFUNGAL AGENTS

(71) Applicants: Hanumant Bapurao Borate, Pune (IN); Sangeshwer Prabhakar Sawargave, Pune (IN); Subhash Prataprao Chavan, Pune (IN); Mohan Anand Chandavarkar, Mumbai (IN); Ramakrishnan Ramacahndran Iyer, Mumbai (IN); Amit Chandrakant Tawte, Mumbai (IN); Deepali Damodar Rao, Mumbai (IN)

(72) Inventors: Hanumant Bapurao Borate, Pune (IN); Sangeshwer Prabhakar Sawargave, Pune (IN); Subhash Prataprao Chavan, Pune (IN); Mohan Anand Chandavarkar, Mumbai (IN); Ramakrishnan Ramacahndran Iyer, Mumbai (IN); Amit Chandrakant Tawte, Mumbai (IN); Deepali Damodar Rao, Mumbai (IN)

(73) Assignees: FDC Limited, Mumbai (IN); Council of Scientific Industrial Research, New Delhi (IN)

( * ) Notice: Subject to any disclaimer, the term of this patent is extended or adjusted under 35 U.S.C. 154(b) by 0 days.

(21) Appl. No.: 14/264,574

(22) Filed: Apr. 29, 2014

(65) Prior Publication Data

US 2014/0249194 A1    Sep. 4, 2014

Related U.S. Application Data

(63) Continuation of application No. PCT/IN2012/000252, filed on Apr. 9, 2012.

(30) Foreign Application Priority Data

Oct. 31, 2011 (IN) .......................... 3063/MUM/2011

(51) Int. Cl.
A01N 43/653 (2006.01)
C07D 253/06 (2006.01)
C07D 409/12 (2006.01)

(52) U.S. Cl.
CPC ......... C07D 409/12 (2013.01); *C07B 2200/07* (2013.01)

(58) Field of Classification Search
CPC ........................... A01N 43/653; C07D 253/06
See application file for complete search history.

(56) References Cited

U.S. PATENT DOCUMENTS 8,236,840 B2 * 8/2012 Borate et al. ................. 514/383
2011/0144171 A1 * 6/2011 Borate et al. ................. 514/383

FOREIGN PATENT DOCUMENTS

WO 2010046912 A2 4/2010

OTHER PUBLICATIONS

Porter, 1991, Pure & Appl. Chem., vol. 63, No. 8, p. 1119-1122.*
"International Search Report for PCT/in2012/00252 dated Oct. 10, 2012".
Fassihi, et al., "Racemates and enantiomers in drug develoopment", International Journal of Pharmaceutics,, May 3, 1993, 1-14.
Testa, et al., "Racemates versus enantiomers in drug development: dogmatism or pragmatism", Chirality, Jan. 1, 1990, 129-133.

* cited by examiner

Primary Examiner — Michael Barker
Assistant Examiner — Karen Cheng
(74) Attorney, Agent, or Firm — Kramer & Amado, P.C.

(57) ABSTRACT

The invention discloses optically active compounds of Formula (1a) or Formula (1b),

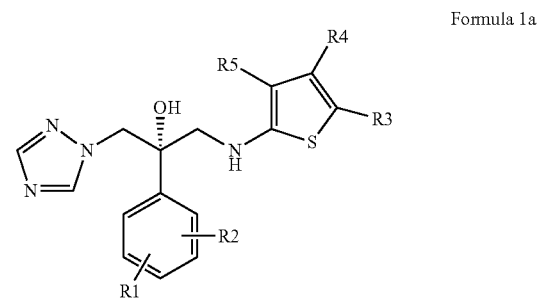
Formula 1a

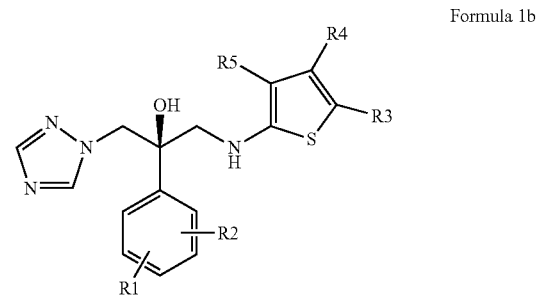
Formula 1b wherein R1 and R2 are independently selected from the group consisting of hydrogen and a halogen selected from the group consisting of fluorine, chlorine, bromine, and iodine; and wherein (a) R3 and R4 are independently selected from the group consisting of hydrogen and an alkyl group having a linear or branched chain having 1 to 20 carbon atoms, or (b) R3 and R4 together form a cycloalkyl ring having 3 to 10 carbon atoms fused to the thiophene ring; and wherein R5 is CN or COOR', where R' is methyl or ethyl. The compounds of Formula (1a) or Formula (1b) may be used in pharmaceutical compositions for treating fungal infections.

23 Claims, No Drawings

OPTICALLY ACTIVE FLUCONAZOLE ANALOGUES CONTAINING THIOPHENES AS ANTIFUNGAL AGENTS

CROSS-REFERENCE TO RELATED APPLICATIONS

This application is a Continuation of parent International Application No. PCT/IN2012/000252, filed on Apr. 9, 2012. The entire disclosure of the prior application is hereby incorporated by reference in its entirety.

FIELD OF INVENTION

The present invention relates to enantiomers of fluconazole analogues containing thiophenes as antifungal agents, which are depicted by Formula (1a) and Formula (1b), and pharmaceutically acceptable salts thereof.

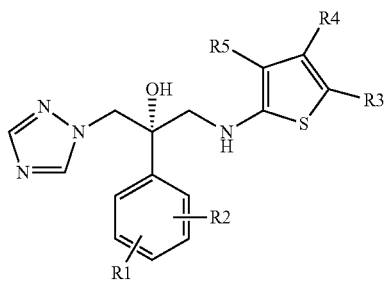

Formula 1a

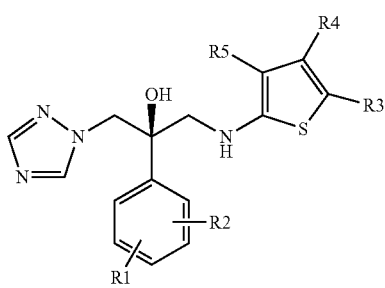

Formula 1b wherein R1 and R2 are independently selected from the group consisting of hydrogen and a halogen selected from the group consisting of fluorine, chlorine, bromine, and iodine; and
wherein (a) R3 and R4 are independently selected from the group consisting of hydrogen and an alkyl group having a linear or branched chain having 1 to 20 carbon atoms, or (b) R3 and R4 together form a cycloalkyl ring having 3 to 10 carbon atoms fused to the thiophene ring; and wherein R5 is CN or COOR', where R' is methyl or ethyl.

The disclosure further relates to a process for preparation of the enantiomers of fluconazole analogues containing thiophenes of Formula (1a) and Formula (1b), and pharmaceutical preparations containing these compounds for prevention and treatment of fungal infections in a subject.

BACKGROUND

Fungus is a type of microorganism that causes fungal infection. A fungal infection is an inflammatory condition in which fungi multiply and invade the skin, the digestive tract, the genitals and other body tissues, particularly the lungs and liver. Fungal infections mainly include superficial and systemic fungal infections. Fungal infections are more common in people taking antibiotics, corticosteroids, immunosuppressant drugs and contraceptives. The fungal infections are prominent in people with endocrine disorders, immune diseases and other conditions such as obesity, AIDS, tuberculosis, major burns, leukemia and diabetes.

The current antifungal agents belong to various groups like polyenes, heterocyclic benzofuran, allylamines, antimetabolites, azoles, glucan synthesis inhibitors, etc. out of which azoles are presently the most extensively used antifungal agents. Azoles are further classified into imidazoles and triazoles. Fluconazole belongs to the family of triazole antifungals. Fluconazole is an important antifungal agent which is orally active and has low toxicity but its extensive use has resulted in emergence of fluconazole-resistant fungal strains. Therefore, it is necessary to meet the long-felt need to develop novel fluconazole analogues which exert high anti-fungal activity against various fungi. The presence of one triazole ring, halogenated phenyl ring and tertiary alcoholic oxygen functionality in azole class of compounds, is necessary for antifungal activity.

The racemic fluconazole analogues containing thiophene moiety of Formula (2) and their excellent fungicidal activities have already been described in the commonly assigned International Patent Publication WO 2010/046912, including methods of preparing such racemic compounds. The racemic compounds have antifungal activity against various fungi.

The racemic compounds have the formula:

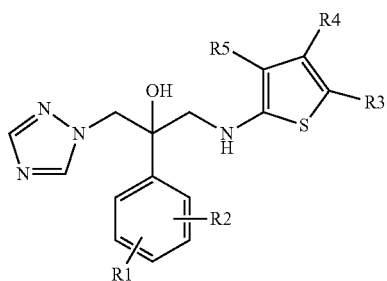

Formula 2

Wherein, R1, R2, R3, R4 and R5 are defined as above.

In the present disclosure, it is shown that one of the enantiomers of a chiral fluconazole analogues containing a thiophene moiety has enhanced antifungal activity, when compared to the corresponding racemic compound. There is a need to develop compounds having high antifungal activity against various fungal strains.

The present disclosure seeks to provide enantiomers of chiral fluconazole analogues of Formula (1a) and Formula (1b) containing thiophene moiety, and processes of making such enantiomers, in effort to come up with antifungal agents having a broad spectrum of antifungal activity.

SUMMARY

Accordingly, to meet the above stated objectives, the present disclosure discloses enantiomers of fluconazole analogues containing thiophene moiety as antifungal agents. The disclosure further shows a process for preparation of these optically active fluconazole analogues, and pharmaceutical preparations containing these compounds, for prevention and treatment of fungal infections.

In various embodiments, optically active fluconazole analogues acting as antifungals proved to have MIC values much smaller than those of either the corresponding racemic compounds or fluconazole.

Various embodiments disclosed herein relate to optically active antifungal compounds of Formula (1a), corresponding to the (S)-configuration, or Formula (1b), corresponding to the (R)-configuration:

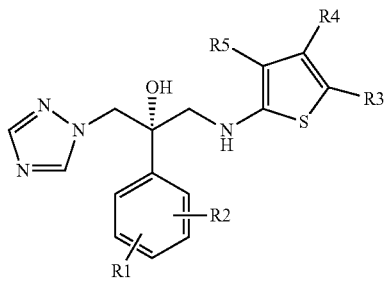

Formula 1a

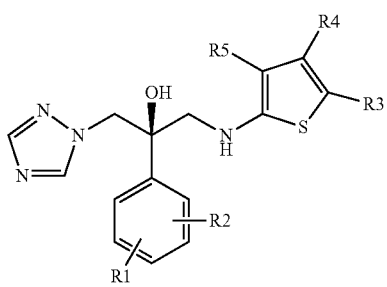

Formula 1b wherein R1 and R2 are independently selected from the group consisting of hydrogen and a halogen selected from the group consisting of fluorine, chlorine, bromine, and iodine; and wherein (a) R3 and R4 are independently selected from the group consisting of hydrogen and an alkyl group having a linear or branched chain having 1 to 20 carbon atoms, or (b) R3 and R4 together form a thiophene-fused cycloalkyl ring having 3 to 10 carbon atoms; and wherein R5 is CN or COOR', where R' is methyl or ethyl.

In various embodiments, the optically active antifungal compounds of Formula (1a) or Formula (1b) have an enantiomeric excess of between about 81% and about 99.9%, between about 97.5% and about 99.9%, or between about 99% and about 99.9%.

Various embodiments disclosed herein relate to a process for preparation of optically active antifungal compounds of Formula (1a) or Formula (1b), by reacting a compound of Formula (3) with a chiral epoxide of Formula (4), in presence of a base and a catalyst:

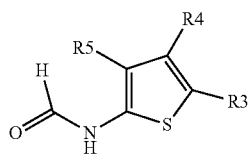

Formula 3

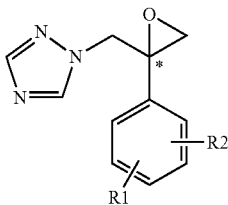

Formula 4 wherein R1, R2, R3, R4 and R5 are defined as set forth above, with regard to compounds of Formula (1a) or Formula (1b); and '*' is used to designate R or S configuration at carbon atom. The base used when reacting a compound of Formula (3) with a chiral epoxide is an organic base, an inorganic base, or mixtures thereof. The inorganic base may be, but is not limited to, potassium carbonate, sodium carbonate, and cesium carbonate. The catalyst used when reacting a compound of Formula (3) with a chiral epoxide may be, but is not limited to, a quaternary ammonium phase transfer catalyst. The phase transfer catalyst may be, but is not limited to, tetrabutylammonium bromide, tertrabutylammonium chloride, triethylbenzylammonium chloride or cetyltrimethylammonium bromide.

Various embodiments disclosed herein relate to a process for preparation of optically active antifungal compounds of Formula (1a) or Formula (1b), by separating a mixture of a compound of Formula (1a) and a compound of Formula (1b) by High Performance Liquid Chromatography (HPLC) using a chiral HPLC column. In various embodiments, the process for preparation of optically active antifungal compounds involves separating a racemic mixture of a compound of Formula (1a) and a compound of Formula (1b) by HPLC.

The HPLC separation may be carried out using an HPLC column having a chiral polysaccharide derivative coated on silica gel as a stationary phase. In various embodiments, the chiral HPLC column may be, but is not limited to, a column containing a stationary phase selected from the group consisting of cellulose tris(3,5-dimethylphenylcarbamate) coated on silica-gel; cellulose tris(4-methylbenzoate) coated on silica-gel; and tris-(3,5-dimethylphenyl)-carbamoyl amylose coated on silica-gel. The chiral HPLC column may be, but is not limited to, a chiral preparative HPLC column.

The HPLC separation may be carried out using a mixture of hydrocarbon(s), alcohol(s) and/or acid(s) as a mobile phase. The mobile phase may comprise from 40% to 90% of at least one hydrocarbon, from 10% to 60% of at least one alcohol, and from 0% to 2% of an acid. The hydrocarbon may be, but is not limited to, pentane, hexane, petroleum ether (60-80 fraction), heptane, iso-octane, cyclohexane, or cyclopentane. The alcohol may be, but is not limited to methanol, ethanol, propan-1-ol, propan-2-ol, butan-1-ol, butan-2-ol, tert-butanol, 3-methyl-1-butanol, 2-methyl-1-propanol, 2-methoxyethanol, or 2-ethoxyethanol. The optional acid may be trifluoroacetic acid.

Various embodiments disclosed herein relate to a pharmaceutical composition for treating fungal infections, comprising an optically active antifungal compound of Formula (1a) or Formula (1b), and at least one pharmaceutical excipient. In some embodiments, the optically active antifungal compound is a compound of Formula (1a), with an enantiomeric excess of between about 81% and about 99.9%, between about 97.5% and about 99.9%, or between about 99% and about 99.9%.

Various embodiments disclosed herein relate to methods of treating fungal infections in a patient in need thereof, by administering a therapeutically effective amount of an optically active antifungal compound of Formula (1a) to said patient, or by administering a therapeutically effective amount of an optically active antifungal compound of Formula (1b) to said patient. In certain embodiments, a therapeutically effective amount of an optically active antifungal compound of Formula (1a) is administered to the patient, where the patient is a mammal.

DETAILED DESCRIPTION

According to the present disclosure, there are provided enantiomers of fluconazole analogues containing thiophene moiety, as depicted in Formula (1a) and Formula (1b). These compounds belong to azole class of antifungal compounds and are analogues of fluconazole, which are active against fungi and used in pharmaceutical preparations as active agents.

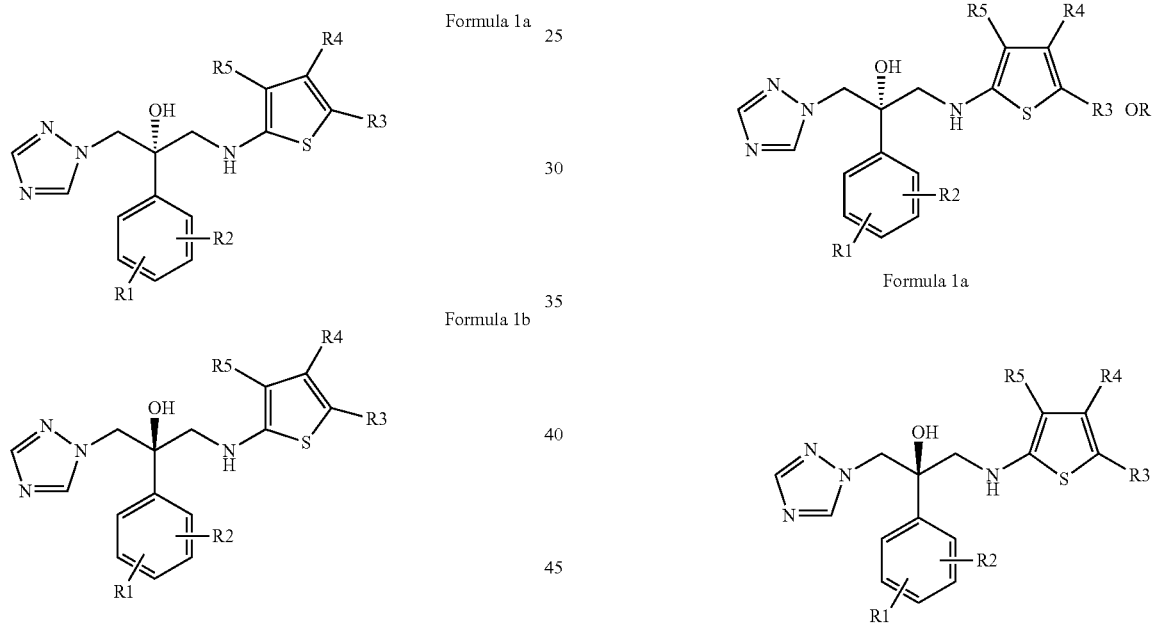

wherein R1 and R2 are independently selected from the group consisting of hydrogen and a halogen selected from the group consisting of fluorine, chlorine, bromine, and iodine; and wherein (a) R3 and R4 are independently selected from the group consisting of hydrogen and an alkyl group having a linear or branched chain having 1 to 20 carbon atoms, or (b) R3 and R4 together form a cycloalkyl ring having 3 to 10 carbon atoms fused to thiophene ring; and wherein R5 is CN or COOR', where R' is methyl or ethyl.

According to another embodiment, the disclosure provides a process for preparation of the compounds of Formula (1a) and Formula (1b). The compounds of Formula (1a) and Formula (1b) of the present disclosure are prepared either by a synthetic process as illustrated in Scheme 1, or by chiral separation using HPLC (High Performance Liquid Chromatography) as illustrated in Scheme 2.

wherein, R1, R2, R3, R4 and R5 are defined as above, and '*' is used to designate R or S configuration at carbon atom.

Accordingly, the process for the preparation of compound of Formula (1a) and Formula (1b) comprises reacting a compound of Formula (3) with a chiral epoxide of Formula (4), in presence of a suitable base and a catalyst. The suitable base used in the present disclosure is selected from various organic or inorganic bases preferably inorganic base such as potassium carbonate, sodium carbonate or cesium carbonate. The suitable catalyst used in the present disclosure is selected from various phase transfer catalysts such as tetrabutylammonium bromide, tertrabutylammonium chloride, triethylbenzylammonium chloride or cetyltrimethylammonium bromide.

Compounds of Formula (1a) and Formula (1b) can also be prepared by chiral separation of racemic compounds of Formula (2) using chiral HPLC in order to obtain desired enantiomers, as shown in Scheme 2. The chiral HPLC is performed using a chiral preparative HPLC column and a mobile phase. Compounds of Formula (2) can be prepared as per the method disclosed in WO 2010/046912.

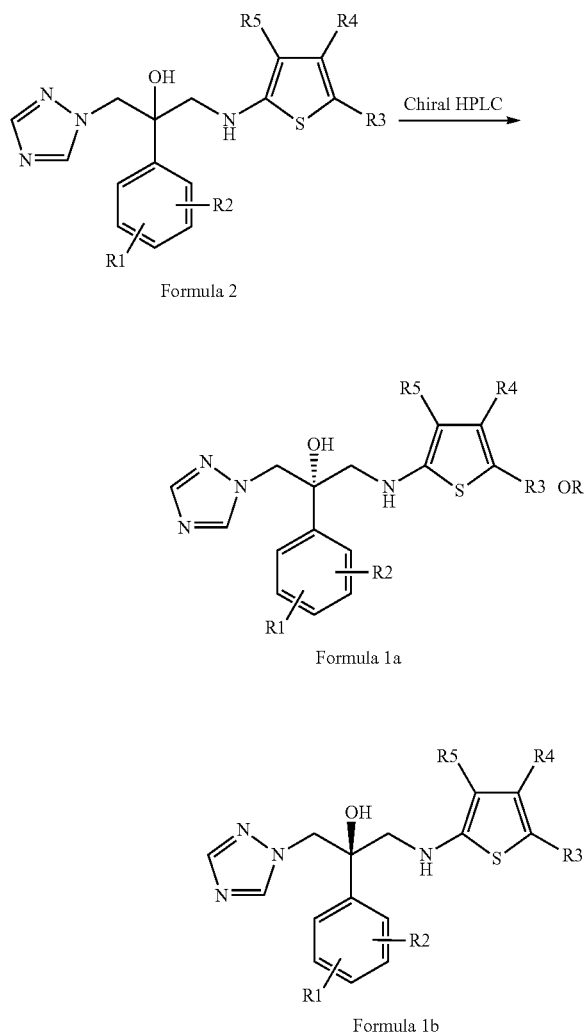

wherein, R1, R2, R3, R4 and R5 are defined as above.

According to the present disclosure, the chiral preparative HPLC column is selected from but not limited to cellulose tris(3,5-dimethylphenylcarbamate) coated on silica-gel, cellulose tris(4-methylbenzoate) coated on silica-gel or tris-(3,5-dimethylphenyl)-carbamoyl amylose coated on silica-gel; and the eluent system is an isocratic system comprising a mixture of hydrocarbon(s), alcohol(s) and/or acid(s).

The hydrocarbons used in the present eluent system are selected from a group consisting of pentane, hexane, heptane, petroleum ether (60-80 fraction), iso-octane, cyclohexane and cyclopentane.

The alcohol used in the present eluent system is selected from the group consisting of methanol, ethanol, propan-1-ol, propan-2-ol, butan-1-ol, butan-2-ol, tert-butanol, 3-methyl-1-butanol, 2-methyl-1-propanol, 2-methoxyethanol and 2-ethoxyethanol.

The acid used in the present eluent system is trifluoroacetic acid.

The ratio of alcohol in the mobile phase of the eluent system ranges from 10% to 60%. The ratio of hydrocarbon in the mobile phase of the eluent system ranges from 40% to 90%. The ratio of trifluoroacetic acid in the mobile phase of the eluent system ranges from 0% to 2%.

In yet another embodiment, the present disclosure provides a pharmaceutical preparation for treating or preventing fungal infections, comprising compounds of Formula (1a) or Formula (1b), in association with at least one pharmaceutically acceptable excipient known in the art.

The pharmaceutical preparations can be selected from various dosage forms such as solid dosage form including tablets, capsules, pellets, powders, soft gelatin capsules and oral liquids. The pharmaceutical compositions can be prepared using conventional techniques well known in the art.

In a further embodiment, the disclosure provides a method for treating or preventing fungal infections in a subject, wherein the said method comprises administering to the subject, therapeutically effective amounts of the compounds of Formula (1a) or Formula (1b) of the present disclosure. The compounds of the present disclosure can also be administered optionally with other actives depending on the disease conditions.

The term "therapeutically effective amount" as used herein, means an amount used in the pharmaceutical preparations to achieve the desired therapeutic effect.

The amount/quantity of the compound used in pharmaceutical compositions of the present disclosure will vary depending upon the body weight of the patient and the mode of administration, and can be of any effective amount to achieve the desired therapeutic effect.

In yet another embodiment, the disclosure describes use of therapeutically effective amounts of compounds of formula 1a or 1b for the treatment or prevention of fungal infections in a subject. The disclosure also describes use of formula 1a and 1b of the present disclosure in the preparation of medicament useful for treating fungal infections in a subject. The subject for the purpose of the disclosure is an animal or a mammal.

The disclosed subject matter is further illustrated with the following examples. These examples should not be construed to limit the scope of the present invention. The features of the present invention will become more apparent from the following description of the preferred embodiments.

The compounds of Formula 1a are depicted in Table 1.
Compounds of Formula (1a)
TABLE 1
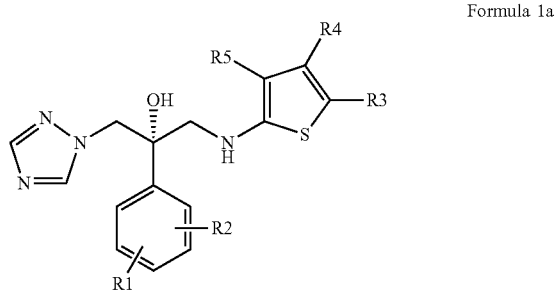
Formula 1a
| Compd No. | R¹ | R² | R³ | R⁴ | R⁵ | Structure |
|---|---|---|---|---|---|---|
| 1a-01 | 2-F | 4-F | methyl | H | CN | 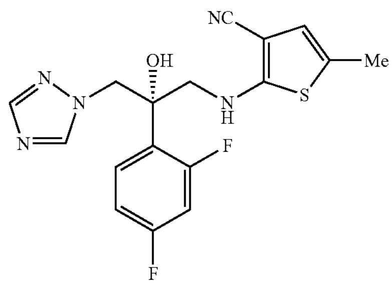 |
| 1a-02 | 2-F | 4-F | propyl | H | CN | 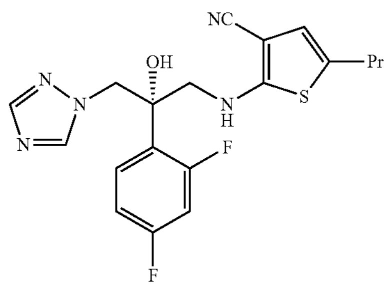 |
| 1a-03 | 2-F | 4-F | butyl | H | CN | 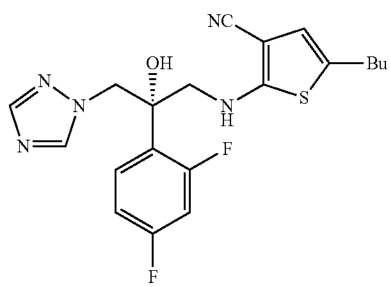 |
| 1a-04 | 2-F | 4-F | pentyl | H | CN | 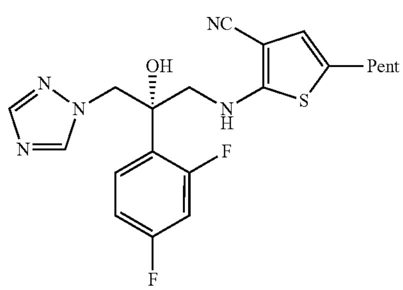 |

The compounds of Formula 1b are depicted in Table 2.
Compounds of Formula (1b)
TABLE 2
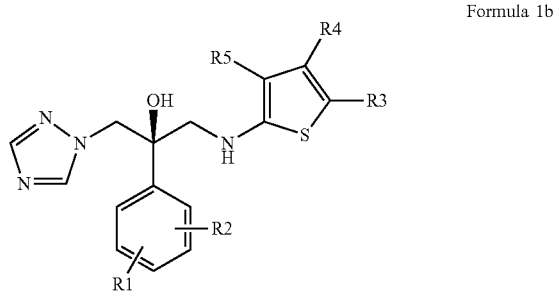
Formula 1b
| Compd No. | R¹ | R² | R³ | R⁴ | R⁵ | Structure |
|---|---|---|---|---|---|---|
| 1b-01 | 2-F | 4-F | methyl | H | CN | 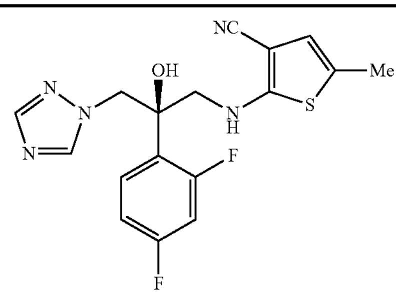 |
| 1b-02 | 2-F | 4-F | propyl | H | CN | 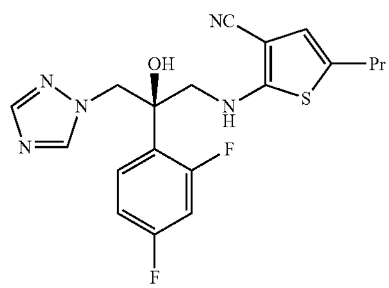 |
| 1b-03 | 2-F | 4-F | butyl | H | CN | 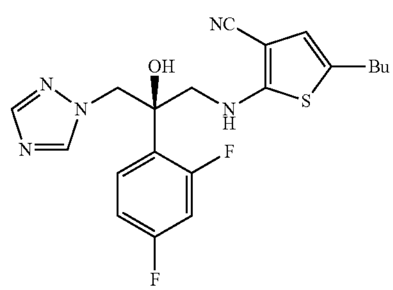 |
| 1b-04 | 2-F | 4-F | pentyl | H | CN | 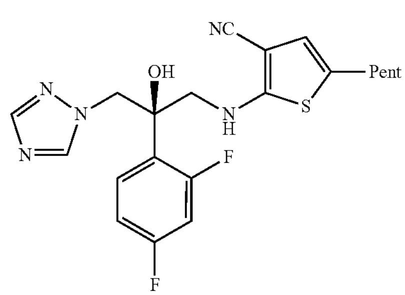 |

The compounds of Formula 2 are depicted in Table 3.
Compounds of Formula (2)
TABLE 3
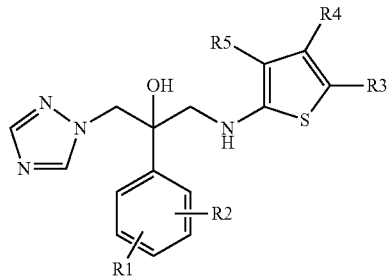
Formula 2
| Compd No. | R¹ | R² | R³ | R⁴ | R⁵ | Structure |
|---|---|---|---|---|---|---|
| 2-01 | 2-F | 4-F | methyl | H | CN | 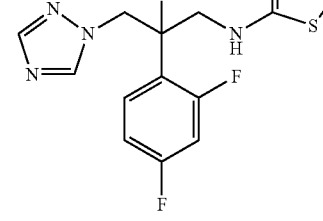 |
| 2-02 | 2-F | 4-F | propyl | H | CN | 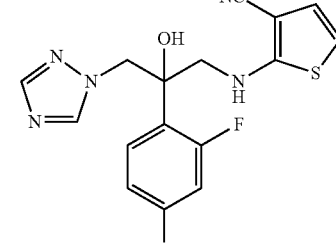 |
| 2-03 | 2-F | 4-F | butyl | H | CN | 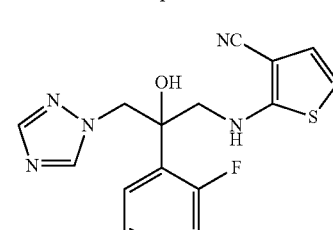 |
| 2-04 | 2-F | 4-F | pentyl | H | CN | 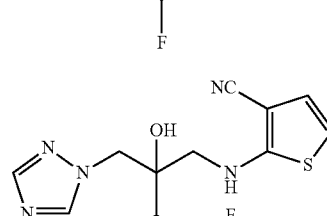 |

The compounds of Formula 3 are depicted in Table 4.

Compounds of Formula (3)

TABLE 4

Formula 3

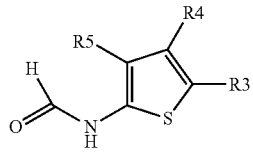

| Compd No. | R³ | R⁴ | R⁵ | Structure |
|---|---|---|---|---|
| 3-01 | methyl | H | CN | NC, H, Me on thiophene |
| 3-02 | propyl | H | CN | NC, H, Pr on thiophene |
| 3-03 | butyl | H | CN | NC, H, Bu on thiophene |
| 3-04 | pentyl | H | CN | NC, H, Pent on thiophene |

The compounds of Formula 4 are depicted in Table 5.

Compounds of Formula (4)

TABLE 5

Formula 4

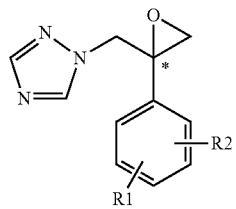

| Compd No. | R¹ | R² | Structure |
|---|---|---|---|
| 4a | 2-F | 4-F | 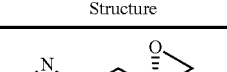 |

TABLE 5-continued

Formula 4

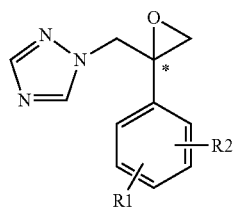

| Compd No. | R¹ | R² | Structure |
|---|---|---|---|
| 4b | 2-F | 4-F | 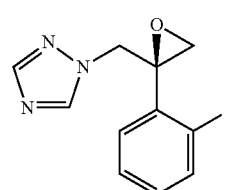 |

EXAMPLES

General Method of Preparation of Compounds of Formula (1a) and Formula (1b) Via Scheme 1

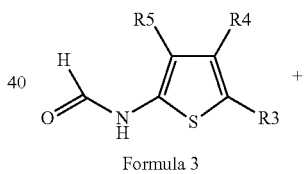

Formula 3

+

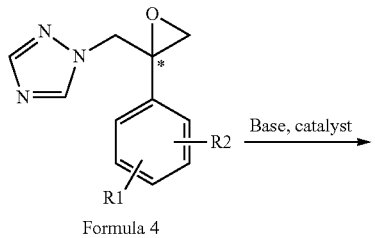

Formula 4

$\xrightarrow{\text{Base, catalyst}}$

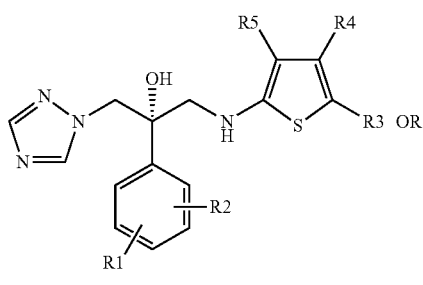 OR

Formula 1a

-continued

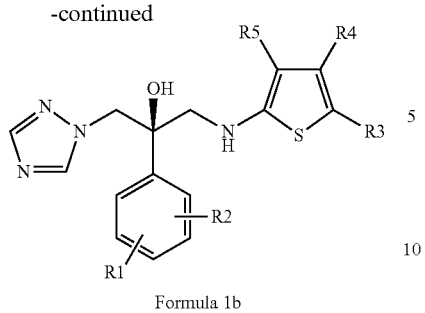

Formula 1b

Wherein, R1, R2, R3, R4 and R5 are defined as above, and "*" is used to designate R or S configuration at carbon atom.

A mixture of compound of Formula 3 (1 equivalent), base (0.5-5 equivalents) and catalyst (0.1-2 equivalents) in a suitable organic solvent was taken in two-necked round bottom flask equipped with a reflux condenser and a guard tube. The mixture was stirred at room temperature for 0.5-4 h and a compound of Formula 4 (1 equivalent) in organic solvent such as ethyl acetate was added. The mixture was stirred under reflux for 5-18 h, cooled, diluted with water, extracted with ethyl acetate, dried over $Na_2SO_4$ and concentrated. Purification by column chromatography afforded the pure product.

Example 1

(S)-2-((2-(2,4-Difluorophenyl)-2-hydroxy-3-(1H-1,2,4-triazol-1-yl)propyl)amino)-5-methylthiophene-3-carbonitrile (1a-01)

A mixture of compound of Formula 3-01 (166 mg, 1 mmol), flame dried potassium carbonate (414 mg, 3 mmol) and tetra-butyl ammonium bromide (322 mg, 1 mmol) in ethyl acetate (10 ml) was taken in two-necked round bottom flask equipped with reflux condenser and guard tube. The mixture was stirred at room temperature for 0.5 h and compound of Formula 4a (244 mg, 1.03 mmol) in ethyl acetate (4 ml) was added. The mixture was stirred under reflux for 13 h, cooled, diluted with water, extracted with ethyl acetate (3×10 ml), dried over $Na_2SO_4$ and concentrated. Purification by column chromatography afforded the pure product; 255 mg (68%); $^1$H NMR (200 MHz, $CDCl_3$): δ 2.28 (s, 3H), 3.64 (d, J=8 Hz, 1H), 3.68 (d, J=8 Hz, 1H), 4.65 (d, J=14 Hz, 1H), 4.87 (d, J=14 Hz, 1H), 5.24 (t, J=8 Hz, 1H), 5.30 (bs, 1H), 6.36 (s, 1H), 6.37-6.87 (m, 2H), 7.45-7.57 (m, 1H), 7.86 (s, 1H), 7.92 (s, 1H); $[α]_D^{25}$=−10° (C=1, methanol); ee 98.99% by chiral HPLC.

Example 2

(S)-2-((2-(2,4-Difluorophenyl)-2-hydroxy-3-(1H-1,2,4-triazol-1-yl)propyl)amino)-5-propylthiophene-3-carbonitrile (1a-02)

The compound of Formula 3-02 (200 mg, 1.03 mmol) in dry ethyl acetate (5 ml) was added to a mixture of flame-dried $K_2CO_3$ (284 mg, 2.06 mmol), tetra-butyl ammonium bromide (TBAB, 332 mg, 1.03 mmol) and dry ethyl acetate (10 ml). Reaction mixture was stirred at 70° C. for 30 min and then epoxide 4a (244 mg, 1.03 mmol) dissolved in dry ethyl acetate (3 ml) was added drop wise over a period of 10 min and stirring was continued for further 15 h at the same temperature. It was then cooled to room temperature, diluted with water (20 ml), extracted with ethyl acetate (3×10 mL), dried over $Na_2SO_4$, concentrated and purified by column chromatography to give pure compound of the Formula 1a-02 (335 mg); Yield: 81%; $^1$H NMR (200 MHz, $CDCl_3$): δ 0.89 (t, J=7 Hz, 3H), 1.43-1.60 (m, 2H), 2.50 (t J=7 Hz, 2H), 3.63 (bs, 2H), 4.67 (d, J=14 Hz, 1H), 4.80 (d, J=14 Hz, 1H), 5.05 (bs, 1H), 6.31 (s, 1H), 6.66-6.82 (m, 2H), 7.41-7.58 (m, 1H), 7.77 (s, 1H), 8.07, (s, 1H); $[α]_D^{25}$=−12° (C=1, THF); ee 99.16% by chiral HPLC.

Example 3

(S)-5-Butyl-2-((2-(2,4-difluorophenyl)-2-hydroxy-3-(1H-1,2,4-triazol-1-yl)propyl)amino)thiophene-3-carbonitrile (1a-03)

The compound of Formula 3-03 (104 mg, 0.5 mmol) in dry ethyl acetate (5 ml) was added to a mixture of flame-dried $K_2CO_3$ (284 mg, 2.06 mmol), tetra-butyl ammonium bromide (TBAB, 32 mg, 0.1 mmol) and dry ethyl acetate (10 ml). Reaction mixture was stirred at 70° C. for 30 min and then epoxide 4a (118 mg, 0.5 mmol) dissolved in dry ethyl acetate (3 ml) was added drop wise over a period of 10 min and stirring was continued for further 20 h at the same temperature. It was then cooled to room temperature, diluted with water (20 ml), extracted with ethyl acetate (3×10 mL), dried over Na$_2$SO$_4$, concentrated and purified by column chromatography to give pure compound of the Formula 1a-03 (131 mg); Yield: 63%; $^1$H NMR (200 MHz, CDCl$_3$): δ 0.88 (t, J=8 Hz, 3H), 1.20-1.40 (m, 2H), 1.46-1.59 (m, 2H), 2.56 (t, J=8 Hz, 2H), 3.61 (d, J=8 Hz, 1H), 3.67 (d, J=8 Hz, 1H), 4.66 (d, J=16 Hz, 1H), 4.81 (d, J=16 Hz, 1H), 5.41-5.49 (m, 2H), 6.32 (s, 1H), 6.69-6.85 (m, 2H), 7.44-7.57 (m, 1H), 7.78 (s, 1H), 7.99 (s, 1H); $[\alpha]_D^{25}$=−10° (C=1, methanol); ee 97.45% by chiral HPLC.

Example 4

(S)-2-((2-(2,4-Difluorophenyl)-2-hydroxy-3-(1H-1, 2,4-triazol-1-yl)propyl)amino)-5-pentylthiophene-3-carbonitrile (1a-04)

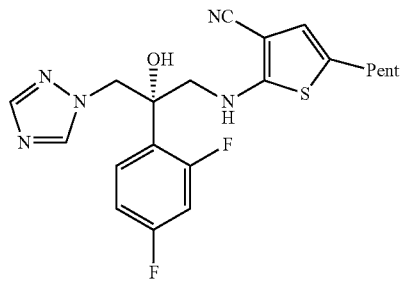

To a mixture of compound of Formula 3-04 (178 mg, 0.8 mmol), flame-dried K$_2$CO$_3$ (552 mg, 4.0 mmol) and tetrabutyl ammonium bromide (TBAB, 32 mg, 0.1 mmol), dry ethyl acetate (10 ml) was added and the reaction mixture was stirred at 65° C. for 20 min and then epoxide 4a (190 mg, 0.8 mmol) dissolved in dry ethyl acetate (5 ml) was added drop wise over a period of 10 min and stirring was continued for further 12 h at the same temperature. It was then cooled to room temperature and extracted with ethyl acetate (3×15 mL) after dilution with water (20 ml). The organic layer was dried over Na$_2$SO$_4$, concentrated and purified by column chromatography to give pure compound of the Formula 1a-04 (270 mg); Yield: 78%; $^1$H NMR (500 MHz, CDCl$_3$): δ 0.90 (t, J=10 Hz, 3H), 1.26-1.35 (m, 4H), 1.52-1.58 (m, 2H), 2.57 (t, J=10 Hz, 2H), 3.62 (d, J=10 Hz, 1H), 3.68 (d, J=10 Hz, 1H), 4.67 (d, J=10 Hz, 1H), 4.86 (d, J=10 Hz, 1H), 5.27-5.31 (m, 2H), 6.36 (s, 1H), 6.75-6.83 (m, 2H), 7.49-7.54 (m, 1H), 7.85 (s, 1H), 7.93 (s, 1H); $[\alpha]_D^{25}$=−12° (C=1, methanol); ee 99.89% by chiral HPLC.

General Method of Preparation of Compounds of Formula (1a) and Formula (1b) Via Scheme 2

Compounds of Formula 2 in Scheme 2 were prepared as described in WO 2010/046912. The racemic compounds of Formula 2 were analyzed by analytical HPLC on chiral column to get separation and to develop the conditions for preparative chiral HPLC in order to isolate the enantiomers in pure form. The racemic compounds of Formula 2 were separated into their S and R enantiomers of Formula (1a) and Formula (1b) respectively, using chiral preparative HPLC. The analytical as well as chiral preparative HPLC was carried out under following general conditions:

| HPLC column | Chiracel-OD-H (DAICEL) | or its equivalent, or Chiracel OJ or its equivalent, or Chiralpak AD or its equivalent

| Mobile Phase | Alcohol: Hydrocarbon or |
| | Alcohol: Hydrocarbon: acid |
| Wavelength | 254 nm |

Example 5

(R)-2-((2-(2,4-Difluorophenyl)-2-hydroxy-3-(1H-1, 2,4-triazol-1-yl)propyl)amino)-5-propylthiophene-3-carbonitrile (1b-02)

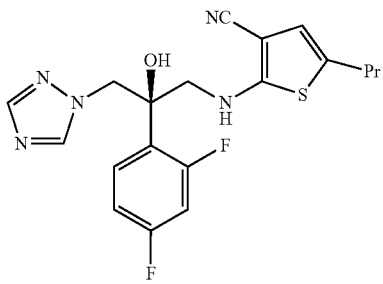

The racemic compound of Formula 2-02 was separated into its S and R enantiomers of Formula (1a-02) and Formula (1b-02) respectively using preparative HPLC under following conditions:

| HPLC column | Kromasil-5-CelluCoat (250 × 4.6 mm) |
| Mobile Phase | iso-Propanol-Pet ether-Trifluoroacetic acid (20:80:0.1) |
| Wavelength | 254 nm |
| Retention time | Formula (1a-02): 30.65 min |
| | Formula (1b-02): 26.36 min |

The retention time, rotation and spectral data of compound of Formula (1a-02) was identical with the sample obtained in Example 2.

The rotation of compound of Formula (1b-02) was $[\alpha]_D^{25}$=+10° (C=1, THF); ee 81.3% by chiral HPLC.

Antifungal Activity Testing:

The compounds of Formula (1a) and (1b) were tested for antifungal activity against various strains of Candida (Candida albicans ATCC 24433, C. albicans ATCC 10231, C. albicans ATCC 2091, C. albicans ATCC 90028, C. glabrata ATCC 90030, C. Krusei ATCC 6258, C. tropicalis ATCC 750), Cryptococcus neoformans ATCC 34664, Aspergillus niger ATCC 16404, Aspergillus fumigatus ATCC 46645 and Fusarium proliferatum ATCC 10052. In vitro evaluation of antifungal activity was performed by determining the minimum inhibitory concentration (MIC) following standard broth dilution methods (CLSI: Reference method for broth dilution antifungal susceptibility testing of yeasts; Approved standard, second edition M27-A2, 2002; CLSI: Reference method for broth dilution antifungal susceptibility testing of filamentous fungi; Approved standard M38-A, 2002) using RPMI 1640 medium buffered to pH 7.0 with MOPS buffer. Known anti-fungal agents like Fluconazole and Amphotericin-B were used as standards. End points were determined after 48 hours visually and by using spectrophotometer wherever necessary. The activity parameters are enumerated in Table 1:

TABLE 1

$MIC_{50}$ obtained by broth dilution method

| Organism | $MIC_{50}$ in µg/ml | | | | | | | | | | |
|---|---|---|---|---|---|---|---|---|---|---|---|
| | AMB | FLU | 2-02 | 1b-02 | 1a-02 | 2-01 | 1a-01 | 2-04 | 1a-04 | 2-03 | 1a-03 |
| C. albicans ATCC 24433 | 0.25 | 0.5 | 0.06 | 0.5 | 0.06 | 0.25 | 0.12 | 0.25 | 0.12 | 0.12 | 0.06 |
| C. albicans ATCC 10231 | 0.5 | 0.5 | 0.12 | 1 | 0.12 | 0.5 | 0.25 | 1 | 0.5 | 0.12 | 0.06 |
| C. albicans ATCC 2091 | 0.5 | 0.5 | 0.12 | 1 | 0.12 | 0.5 | 0.25 | 1 | 0.5 | 0.25 | 0.12 |
| C. albicans ATCC 90028 | 0.5 | 0.5 | 0.12 | 0.5 | 0.06 | 0.5 | 0.25 | 0.5 | 0.25 | 0.12 | 0.06 |
| C. glabrata ATCC 90030 | 0.25 | 4 | 0.12 | 0.5 | 0.12 | 0.25 | 0.12 | 0.25 | 0.12 | 0.12 | 0.06 |
| C. krusei ATCC 6258 | 0.5 | 64 | 8 | >8 | 8 | 64 | 32 | 8 | 4 | 8 | 4 |
| C. tropicalis ATCC 750 | 0.5 | 2 | 2 | >8 | 2 | 4 | 2 | 2 | 1 | 1 | 0.5 |
| C. neoformans ATCC 34664 | 0.5 | 2 | 1 | 8 | 0.5 | 4 | 2 | 2 | 1 | 1 | 0.5 |
| A. niger ATCC 16404 | 0.25 | >128 | 4 | >8 | 8 | >64 | >64 | >8 | >8 | >4 | >4 |
| A. fumigatus ATCC 46645 | 0.5 | >128 | >16 | 8 | >16 | >64 | >64 | >8 | >8 | >4 | >4 |
| F. proliferatum ATCC 10052 | 2 | >128 | >16 | >128 | >16 | >64 | >64 | >8 | >8 | >4 | >4 |

*For azoles and NCEs: For Fluconazole and the NCEs, MIC is recorded as the concentration exhibiting more than 50% inhibition as compared to the positive control.
For Amphotericin B: MIC is recorded as the concentration exhibiting complete inhibition.

It was observed that one of the enantiomers of each compound was more active than the corresponding racemic compound.

It will be evident to those skilled in the art that the disclosed subject matter is not limited to the details of the foregoing illustrative examples and that the present invention may be embodied in other specific forms without departing from the essential attributes thereof. It is therefore desired that the present embodiments and examples be considered in all respects as illustrative and not restrictive.

We claim:

1. An optically active antifungal compound having Formula (1b);

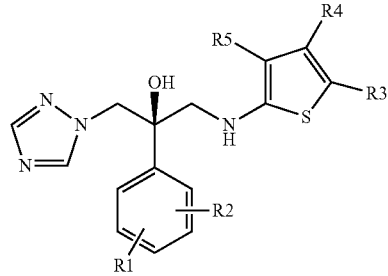

Formula 1b wherein R1 and R2 are independently selected from the group consisting of hydrogen and a halogen selected from the group consisting of fluorine, chlorine, bromine, and iodine; and
wherein (a) R3 and R4 are independently selected from the group consisting of hydrogen and an alkyl group having a linear or branched chain having 1 to 20 carbon atoms, or (b) R3 and R4 together form a thiophene-fused cycloalkyl ring having 3 to 10 carbon atoms; and
wherein R5 is CN,
said optically active antifungal compound having an enantiomeric excess of between about 81% and about 99.9%;
wherein said optically active compound has antifungal activity against A. fumigates.

2. An optically active antifungal compound having Formula (1a);

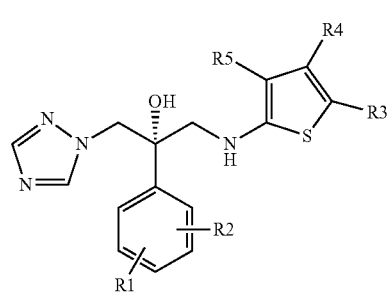

Formula 1a wherein R1 and R2 are independently selected from the group consisting of hydrogen and a halogen selected from the group consisting of fluorine, chlorine, bromine, and iodine; and
wherein (a) R3 and R4 are independently selected from the group consisting of hydrogen and an alkyl group having a linear or branched chain having 1 to 20 carbon atoms, or (b) R3 and R4 together form a thiophene-fused cycloalkyl ring having 3 to 10 carbon atoms; and
wherein R5 is CN or COOR', where R' is methyl or ethyl.

3. The optically active antifungal compound of claim 2, having an enantiomeric excess of between about 97.5% and about 99.9%.

4. A process for preparation of the optically active antifungal compound of claim 2, comprising:
reacting a compound of Formula (3) with a chiral epoxide of Formula (4), in the presence of a base and a catalyst;

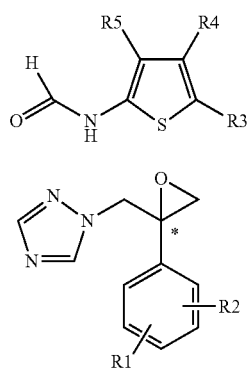

Formula 3

Formula 4 wherein R1, R2, R3, R4 and R5 are defined as in claim 2.

5. The process as claimed in claim 4, wherein the base is selected from the group consisting of at least one organic base, at least one inorganic base, and mixtures thereof.

6. The process as claimed in claim 5, wherein the inorganic base is selected from the group consisting of potassium carbonate, sodium carbonate, and cesium carbonate.

7. The process as claimed in claim 4, wherein the catalyst is a quaternary ammonium phase transfer catalyst.

8. The process as claimed in claim 4, wherein the catalyst is a phase transfer catalyst selected from the group consisting of tetrabutylammonium bromide, tertrabutylammonium chloride, triethylbenzylammonium chloride and cetyltrimethylammonium bromide.

9. A process for preparation of the optically active antifungal compound of claim 2, comprising:

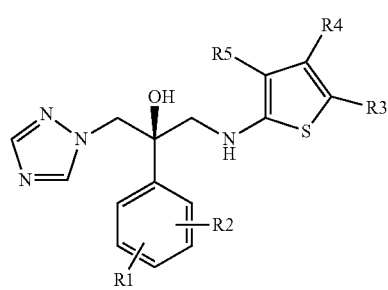

Formula 1b separating a mixture of said compound of Formula (1a) and a compound of Formula (1b) by High Performance Liquid Chromatography (HPLC) using a chiral HPLC column.

10. The process of claim 9, wherein said chiral HPLC column is a chiral HPLC column selected from the group consisting of:
cellulose tris (3,5-dimethylphenylcarbamate) coated on silica-gel,
cellulose tris (4-methylbenzoate) coated on silica-gel; and
tris-(3,5-dimethylphenyl)-carbamoyl amylose coated on silica-gel.

11. The process of claim 9, wherein said chiral HPLC column is a chiral preparative HPLC column.

12. The process of claim 9, wherein said separating is carried out using a mobile phase comprising at least one hydrocarbon, at least one alcohol, and an optional acid.

13. The process of claim 9, wherein said separating is carried out using a mobile phase comprising from 40% to 90% of at least one hydrocarbon, from 10% to 60% of at least one alcohol, and from 0% to 2% of an acid.

14. The process of claim 12, wherein the hydrocarbon is selected from the group consisting of pentane, hexane, petroleum ether (60-80 fraction), heptane, iso-octane, cyclohexane, and cyclopentane.

15. The process of claim 12, wherein the alcohol is selected from the group consisting of methanol, ethanol, propan-1-ol, propan-2-ol, butan-1-ol, butan-2-ol, tert-butanol, 3-methyl-1-butanol, 2-methyl-1-propanol, 2-methoxyethanol, and 2-ethoxyethanol.

16. The process of claim 12, wherein the optional acid is trifluoroacetic acid.

17. A pharmaceutical composition for treating fungal infections, comprising:
the optically active antifungal compound of claim 2; and
at least one pharmaceutical excipient.

18. The pharmaceutical composition of claim 17,
wherein said optically active antifungal compound has an enantiomeric excess of between about 97.5% and about 99.9%.

19. A method of treating fungal infections in a patient in need thereof, comprising:
administering a therapeutically effective amount of the optically active antifungal compound of claim 2 to said patient.

20. A method of treating fungal infections in a patient in need thereof, comprising:
administering a therapeutically effective amount of the pharmaceutical composition of claim 17 to said patient.

21. A method of treating fungal infections in a patient in need thereof, comprising:
administering a therapeutically effective amount of the pharmaceutical composition of claim 18 to said patient.

22. The method according to claim 19, wherein the patient is a mammal.

23. The optically active antifungal compound of claim 2, wherein said optically active antifungal compound has antifungal activity against at least one of *C. albicans, C. glabrata, C. tropicalis, C. neoformans* and *C. krusei*.

* * * * *